United States Patent [19]

Reiling et al.

[11] Patent Number: 5,466,857

[45] Date of Patent: Nov. 14, 1995

[54] PROCESS FOR REDUCTION OF WASTE MATERIAL DURING MANUFACTURE OF ACRYLONITRILE

[75] Inventors: Vincent G. Reiling, Shaker Heights, Ohio; Jeffrey E. Rinker, Victoria, Tex.; Timothy R. McDonel, Brecksville, Ohio; Joseph C. Sarna, Victoria, Tex.

[73] Assignee: The Standard Oil Company, Cleveland, Ohio

[21] Appl. No.: 288,118

[22] Filed: Aug. 10, 1994

[51] Int. Cl.$^6$ ............ C07C 253/18; C07C 253/24; C07C 253/26

[52] U.S. Cl. .......... 558/319; 558/320; 558/321; 558/322; 558/323; 558/324; 558/325; 558/326

[58] Field of Search ............... 558/319, 320

[56] References Cited

U.S. PATENT DOCUMENTS

| | | | |
|---|---|---|---|
| 3,911,089 | 10/1975 | Shiraishi et al. | 423/376 |
| 4,485,079 | 11/1984 | Brazdil, Jr. et al. | 423/376 |
| 4,873,215 | 10/1989 | Brazdil et al. | 502/202 |
| 5,288,473 | 2/1994 | Shaw et al. | 558/319 |

FOREIGN PATENT DOCUMENTS

| | | |
|---|---|---|
| 1032747 | 5/1989 | China . |
| 54-87474 | 4/1979 | Japan . |

*Primary Examiner*—Joseph Paul Brust
*Attorney, Agent, or Firm*—Michael F. Esposito; David J. Untener

[57] ABSTRACT

A process for the reduction in the amount of waste material generated during the manufacture of acrylonitrile comprising introducing an additional amount of oxygen containing gas, preferably air, in the substantial absence of any oxygenate compounds, into the upper portion of the fluid bed reactor to react with at least some of the unreacted ammonia to reduce the amount of unreacted ammonia present in the reactor effluent.

18 Claims, No Drawings

5,466,857

PROCESS FOR REDUCTION OF WASTE MATERIAL DURING MANUFACTURE OF ACRYLONITRILE

BACKGROUND OF THE INVENTION

The present invention is directed to substantial reduction of unreacted ammonia and the corresponding reduction in ammonium sulfate and resulting waste products produced from the unreacted ammonia during the manufacture of acrylonitrile by the direct ammoxidation of an unsaturated or saturated hydrocarbon, preferably propylene or propane, ammonia and oxygen in a fluid bed reactor containing an ammoxidation catalyst. In particular, the present invention is directed to the addition of an oxygen containing gas, preferably air, at a specific location in the fluidized bed reactor during the manufacture of acrylonitrile to reduce substantially the amount of ammonia remaining in the gaseous effluents exiting the fluidized bed reactor during the manufacture of acrylonitrile. This process is carried out in the absence of any additional oxygenated hydrocarbon compound such as methanol. This substantial reduction in the generation of ammonium sulfate during the practice of the manufacture of acrylonitrile leads to significant environmental and economic advantages.

There are several patents which are directed to the injection of methanol into a fluid bed reactor to produce hydrogen cyanide. In addition, these references further disclose the injection of methanol into an acrylonitrile fluid bed reactor to produce hydrogen cyanide while manufacturing acrylonitrile. For example, U.S. Pat. Nos. 3,911,089 and 4,485,079 each teach the ammoxidation of methanol to produce hydrogen cyanide by injection of methanol into a fluid bed reactor containing an ammoxidation catalyst suitable for the manufacture of acrylonitrile. Moreover, Japanese Patent Applications 74-87474, 79-08655 and 78-35232 all are related to similar methods of increasing or making hydrogen cyanide during the manufacture of acrylonitrile. Japanese Patent Application 74-87874 also suggests that a secondary effect of their procedure is the decrease of the amount of sulfuric acid used for neutralization. All of these patents are primarily concerned with the production of additional hydrogen cyanide. Finally, U.S. Pat. No. 5,288,473 and copending applications U.S. Ser. No. 08/187,425 filed Jan. 26, 1994 and U.S. Ser. No. 08/104,752 filed Aug. 11, 1993, all assigned to the assignee of the present invention, are directed to the substantial reduction of the amount of unreacted ammonia exiting the fluid bed reactor which utilized oxygenate compounds such as methanol while Chinese Patent CN 1032747 to Sun et al. discloses multi-staged air feed to a reactor to increase acrylonitrile conversion.

The present invention is directed to a specific procedure for injection of an oxygen containing gas, preferably air, into the fluid bed reactor to obtain a substantial reduction in the amount of unreacted ammonia exiting the fluid bed reactor during the manufacture of acrylonitrile without any decrease in the acrylonitrile yield. The process is performed in the absence of any oxygenated hydrocarbon compounds such as methanol.

SUMMARY OF THE INVENTION

It is a primary object of the present invention to substantially reduce the amount of ammonium sulfate generated during the manufacture of acrylonitrile.

It is a further object of the present invention to substantially reduce the amount of unreacted ammonia exiting the reactor effluents during the manufacture of acrylonitrile.

Additional objects, advantages and novel features of the invention will be set forth in part in the description that follows, and in part will become apparent to those skilled in the art upon examination of the following or may be learned by practice of the invention. The objects and advantages of the invention may be realized and obtained by means of the instrumentalities and combinations particularly pointed out in the appended claims.

To achieve the foregoing objects in accordance with the purpose of the present invention as embodied and described herein, the method of the present invention comprises introducing into the lower portion of a fluid bed reactor ammonia, an oxygen containing gas and a hydrocarbon selected from the group consisting of propylene and propane, to react in the presence of a fluid bed catalyst to produce acrylonitrile, introducing an additional amount of oxygen containing gas substantially free of any oxygenate compound into the upper portion of the fluid bed reactor at a point where the additional oxygen does not substantially affect the reaction to produce acrylonitrile but reacts with at least some of the unreacted ammonia and propylene present in the reactor to reduce the amount of free ammonia present in the reactor effluent exiting said reactor, passing the reactor effluent containing acrylonitrile into a quench column to cool the reactor effluent with water to remove unwanted impurities and recovering the acrylonitrile from the quench column. Two additional benefits obtained from the practice of the present invention are that (1) no additional acrolein, an undesirable by-product of acrylonitrile production, is manufactured and (2) additional hydrogen cyanide, a desirable by-product in most cases, is produced.

In a preferred embodiment of the process of the present invention the oxygen containing gas is air.

In a preferred embodiment of the process of the present invention the point of injection of the additional oxygen containing gas into the reactor is at a point above at least 50 percent of the calculated expanded fluid catalytic bed height, preferably above at least 70 percent of the calculated expanded bed height, most preferably above 85 percent, especially preferred being above 90 percent.

In another preferred embodiment of the present invention the additional oxygen containing gas is introduced above 100 percent of the calculated expanded bed height.

In another aspect of the present invention as embodied and broadly described herein, the method of the present invention comprises introducing ammonia, an oxygen containing gas and a hydrocarbon selected from the group consisting of propylene and propane into the lower portion of a fluid bed reactor containing a fluid bed ammoxidation catalyst to react in the presence of said catalyst to produce acrylonitrile wherein the improvement comprises introducing an additional amount of an oxygen containing gas, preferably air, in the absence of any oxygenate compounds into the upper portion of the fluid bed reactor at a point where the oxygen does not substantially affect the reaction of the hydrocarbon, ammonia and oxygen containing gas to produce acrylonitrile but reacts with at least some of the unreacted ammonia present in the reactor to reduce the amount of ammonia exiting the reactor.

In a preferred embodiment of the present invention the additional oxygen containing gas is injected into the upper portion of the reactor at a location above at least 70 percent of the calculated expanded fluid catalytic bed height.

In a still further preferred embodiment of the present invention the additional oxygen containing gas is injected into the upper portion of the fluid bed reactor at a location above at least 80 percent of the calculated expanded fluid catalytic bed height.

In a still further preferred embodiment of the present invention the additional oxygen containing gas is injected into the upper portion of the fluid bed reactor at a location above at least 90 percent of the calculated expanded fluid catalytic bed height.

In another preferred embodiment of the present invention the amount of additional oxygen containing gas injected into the fluid bed reactor is sufficient to react with at least 15 percent of the unreacted ammonia present in the upper portion of the fluid bed reactor, preferably at least 25 percent, especially preferred being at least 40 percent.

The term oxygenate compounds as defined for purposes of this invention include carboxylic acids, ketones, alcohols, esters or mixtures thereof. The present invention is characterized by the fact that no significant amounts of these materials are present during the practice of the process of the present invention.

The significance of the process in the present invention is that it provides a simple and economic procedure for the substantial reduction of ammonia breakthrough (i.e. unreacted $NH_3$) in a fluid bed reactor along with the attendant advantages of (1) reducing ammonium sulfate as a by-product during the manufacture of acrylonitrile, (2) achieving a reduction of $NH_3$ breakthrough without the use of costly oxygenate compounds and (3) achieving a reduction of $NH_3$ breakthrough without producing additional amounts of undesirable by-products. This can lead to significant economic advantages in the practice of the acrylonitrile process if one cannot practice deepwell injection. Currently, the waste stream emanating from the quench column contains $(NH_4)_2SO_4$ in a fairly high concentration which makes the disposal of these streams in an economic and environmental acceptable manner difficult. The minimization of this ammonium salt from this stream can make these streams acceptable to treatment by waste treatment procedures which do not require severe conditions or expensive materials of construction (e.g. incineration), or if deepwell injection is not available leading to significant economic and environmental advantages.

Reference will now be made in detail to the present preferred embodiment of the invention.

DETAILED DESCRIPTION OF THE INVENTION

The present invention reduces the production of ammonium sulfate generated during the manufacture of acrylonitrile by adding an additional amount of oxygen containing gas, preferably air, substantially free of any oxygenate compounds, preferably in the absence of any oxygenate compounds, to the fluid bed reactor at a location which allows for the reaction of at least some of the excess ammonia in the reactor with the additional oxygen without substantially affecting the efficiency of the acrylonitrile production. It is important to appreciate that the injection of the oxygen containing gas to the upper portion of the reactor is an actual injection of an additional amount of oxygen into the reactor above the amount added to the lower portion of the reactor during normal operating conditions used to produce acrylonitrile. That is, if the normal operating conditions required an air to propylene ratio of 9.5:1 in the bottom of the reactor, this ratio would be maintained while additional oxygen would be injected into the reactor at the upper location. The reduction of ammonium sulfate from the waste stream emanating from the quench column of an acrylonitrile plant can dramatically improve the environmental impact and economics associated with the practice of the acrylonitrile process.

In the preferred practice of the present invention, air is injected into the fluid bed reactor in the upper portion of the reactor in the catalyst zone (at least 50 percent of the expanded bed height) or above (i.e. a height above 100 percent of the expanded catalyst bed height) from a sparger at a position where it will have an opportunity to react with a substantial amount of the excess ammonia but not be competitive with the main propylene ammoxidation reaction occurring in the lower portion of the catalyst bed. For the purposes of the present invention, the term fluid bed reactor is intended to not only encompass conventional fluid bed reactors but also any reactor capable of maintaining the catalyst in a fluid state such as circulating fluid bed reactors, transport line reactors, riser reactors or recycle reactors. The additional oxygen can be injected into the reactor in any direction although a downward angle is preferred. The air sparger may be constructed from conventional materials (e.g. steel/steel alloys) with the number of nozzles being sufficient to allow for good mixing without affecting flow distribution in the reactor.

In another preferred embodiment of the present invention, the location of the additional oxygen containing gas should be at a level calculated at 70 percent of the level of the expanded catalyst bed height, preferably 80 to 90 percent of the expanded catalyst bed height, most preferably being over 90 percent of expanded catalyst bed height. The term expanded catalyst bed height as used in this application means the catalyst bed height while the catalyst is in the fluidized bed state. That is, the bed height when the gaseous components are present in the fluidized bed reactor and mixing with catalyst.

Each propylene/propane ammoxidation catalyst operates at somewhat different feed ratios and operating conditions for maximum acrylonitrile yield and/or economic considerations. The amount of excess ammonia exiting the reactor from propylene ammoxidation reactor will vary somewhat depending on the catalyst used. The level of additional oxygen containing gas to be added will vary according to the catalyst types and the nature of the reactor. Accordingly, in the practice of the present invention the amount of additional oxygen containing gas injected into the reactor will be dictated by the conditions and the catalyst used. Typically, any ammoxidation catalyst may be utilized in the practice of the present invention although catalysts which operate under a conventional oxygen/propylene ratio (e.g. above 9.3:1) are preferred. For example, catalyst such as those disclosed in U.S. Pat. Nos. 3,642,930; 4,485,079; 3,911,089; 4,873,215; 4,877,764; Japanese Patent Application Nos. 74-87474 and 78-35232 are suitable for the practice of the present invention and are incorporated herein by reference.

As stated previously, each propylene/propane ammoxidation catalyst will operate at somewhat different feed ratios and operating conditions. During the practice of the process of the present invention the standard operating condition at which the existing propylene/propane catalyst has been operated should not have to be changed but can be changed depending upon feed and catalyst conditions. Conventional operating condition and feed ratio for the manufacture of acrylonitrile as set forth in U.S. Pat. Nos. 3,911,089 and 4,873,215 are suitable and herein incorporated by reference.

For purposes of illustration only, the following examples are set forth to describe the process of the present invention.

EXAMPLE 1

Approximately 12.5 tons of a propylene ammoxidation catalyst was charged to a fluidized bed acrylonitrile reactor. After several days onstream, feeds of air/ammonia/propylene in the mole ratio of 9.3/1.21/1.0 were passed through the catalyst bed at 813°F. reactor bed temperature, 12 psig top pressure at a weight hourly space velocity (WWH) of 0.085 hr-1. Twenty-four hours after adjustment of feed ratios and reactor temperature, baseline recovery run (See Table 1 below) indicated propylene conversions of 98.1 percent, per pass conversions to acrylo 80.49 percent, to HCN 4.98 percent, to acrolein 0.7 percent, to acrylic acid 1.3 percent. Notably, 8 percent of the feed ammonia was burning, with ammonia breakthrough of 0.22 g/scf and sulfuric acid usage in downstream quench operation of 0.22 gpm to neutralize excess ammonia.

EXAMPLE 2

At the same conditions of Example 1, and with no methanol (oxygenate) vapor injected, air was injected through an air sparger at a position in the bed equal to 90 percent of the catalyst's expanded bed height, at dilute air to propylene molar ratio of 0.52. Recovery run (See Table 1 below) gave 99.1 percent $C_3=$ total conversion, 80.5 percent PPC to acrylo, 5.43 percent PPC to HCN, 0.6 percent PPC to acrolein, and 1.3 percent PPC to acrylic acid from propylene. Notably, 7 percent of feed ammonia was burned, and sulfuric acid usage dropped from 0.22 to 0.16 gpm, or 27 percent ammonia breakthrough reduction.

EXAMPLE 3

At the same conditions of Example 2, and with no methanol (oxygenate) vapor injected, air was injected through a separate air sparger at a position in the bed equal to 90 percent of the catalyst's expanded bed height, at dilute air to propylene molar ratio (DPAR) of 0.51. The bottom air/$C_3=$ molar ratio was then decreased from 9.3 to 9.1 to see if the total air/$C_3=$ could be lowered without penalizing AN or HCN yield while still reducing sulfuric acid consumption. Recovery run (See Table 2 below) gave 99.2 percent $C_3=$ total conversion, 79.9 percent PPC to acrylo, 5.6 percent PPC to HCN, 0.6 percent PPC to acrolein, and 1.3 percent PPC to acrylic acid from propylene. Notably, 13 percent of feed ammonia was burned, and sulfuric acid usage dropped from 0.22 to 0.17 gpm, or 23 percent ammonia breakthrough reduction compared to without separate air (See Table 2 below). This showed the total air/$C_3=$ ratio could be lowered from 10 to 9.48 without significant deterioration of AN or HCN yield, lessening the penalty for a higher dilute phase air ratio.

TABLE 2

| Ex. No. | DPAR* mol air/ mol $C_3=$ | $H_2SO_4$ (gpm) | % ABR | $NH_3$ B.T. (g/scf) | Acrylo % PPC | HCN ($C_3=$) % PPC | Acrolein % PPC | Total $C_3=$ % | Total Air/$C_3=$ Ratio |
|---|---|---|---|---|---|---|---|---|---|
| 1 | 0 | 0.22 | 0 | 0.22 | 80.49 | 4.98 | 0.73 | 98.1 | 9.286 |
| 3 | 0.51 | 0.17 | 27 | 0.17 | 79.93 | 5.45 | 0.56 | 99.2 | 9.483 |

EXAMPLES 4 TO 9

The next set of experiments was directed at quantifying the benefits of separate air addition as a function of amount of air added, all other conditions being constant. At the same conditions of Example 1, except feeds of air/ammonia/propylene in the mole ratio of 9.4/1.22/1.0, initial baseline and final baseline (Examples 4 and 5, Table 3 below) indicated propylene conversions of 98.7 percent, per pass conversions to acrylo 80.7 percent, to HCN 5.1 percent, to acrolein 0.8 percent, to acrylic acid 1.7 percent from propylene. Notably, 5 percent of the feed ammonia was burning, with ammonia breakthrough of 0.18 g/scf and sulfuric acid usage in downstream quench operation of 0.17 gpm to neutralize excess ammonia. With no methanol (oxygenate) vapor injected, air was injected through a separate air sparger at a position in the bed equal to 90 percent of the catalyst's expanded bed height, at dilute air to propylene molar ratios of 0.1, 0.2, 0.4 and 0.6. An average of four recovery runs (Examples 6 to 9, Table 3 below) at increasing DPA ratios gave an average 99.2 percent $C_3=$ total conversion, 80.7 percent PPC to acrylo, 5.4 percent PPC to HCN, 0.8 percent PPC to acrolein, and 1.5 percent PPC to acrylic acid from propylene. Notably, 15 percent of feed ammonia was burned, and sulfuric acid usage dropped from 0.17 gpm (0 percent ammonia breakthrough (ABR)) to 0.12 gpm (30

TABLE 1

| Ex. No. | DPAR* mol air/ mol $C_3=$ | $H_2SO_4$ (gpm) | % ABR | $NH_3$ B.T. (g/scf) | Acrylo % PPC | HCN ($C_3=$) % PPC | Acrolein % PPC | Total $C_3=$ % | Total Air/$C_3=$ Ratio |
|---|---|---|---|---|---|---|---|---|---|
| 1 | 0 | 0.22 | 0 | 0.22 | 80.49 | 4.98 | 0.73 | 98.1 | 9.286 |
| 2 | 0.52 | 0.16 | 27 | 0.16 | 80.54 | 5.43 | 0.6 | 99.1 | 9.959 |

Dilute Phase Air Ratio percent ABR) to 0.10 (40 percent ABR) as dilute phase air addition was increased. The relationship between dilute phase air to propylene ratio and sulfuric acid usage, all other reactor conditions being constant (e.g., bottom air/$C_3=$ ratio, $NH_3/C_3=$ ratio, catalyst bed temperature, reactor top pressure and catalyst inventory) is set forth below in Table 3.

increased, relative to baseline acid usage at 1.22 ammonia to propylene ratio. The relationship between dilute phase air to propylene ratio and sulfuric acid usage, all other reactor conditions being constant (e.g., bottom air/$C_3=$ ratio, $NH_3/C_3=$ ratio, catalyst bed temperature, reactor top pressure and catalyst inventory) is set forth in Table 4 below:

TABLE 3

| Ex. No. | DPAR* mol air/ mol $C_3=$ | $H_2SO_4$ (gpm) | % ABR | $NH_3$ B.T. (g/scf) | Acrylo % PPC | HCN ($C_3=$) % PPC | Acrolein % PPC | Total $C_3=$ % | Total Air/$C_3=$ Ratio |
|---|---|---|---|---|---|---|---|---|---|
| Baseline | | | | | | | | | |
| 4 | 0 | 0.17 | 0 | 0.18 | 80.90 | 5.08 | 0.72 | 98.9 | 9.46 |
| 5 | 0 | 0.17 | 0 | 0.08 | 80.43 | 5.11 | 0.85 | 98.6 | 9.35 |
| Dilute Phase Air | | | | | | | | | |
| 6 | 0.10 | 0.13 | 24 | 0.09 | 80.77 | 5.20 | 0.83 | 99.1 | 9.47 |
| 7 | 0.20 | 0.12 | 29 | 0.12 | 80.88 | 5.39 | 0.62 | 99.2 | 9.73 |
| 8 | 0.40 | 0.12 | 29 | 0.12 | 80.60 | 5.56 | 0.78 | 99.2 | 9.86 |
| 9 | 0.61 | 0.10 | 41 | 0.08 | 80.62 | 5.37 | 0.79 | 99.2 | 10.08 |

EXAMPLES 10 TO 14

The next set of experiments was directed at demonstrating applicability of dilute phase air (additional air at elevated point in reactor) over a wider range of ammonia ratio. The experiments illustrated in Examples 4 to 9 were repeated except at a lowered ammonia to propylene ratio of 1.17. At the same conditions of Examples 4 to 9, except feeds of air/ammonia/propylene of molar ratio 9.3/1.17/1.0, average of two baseline recovery runs (Examples 10 and 11, Table 4 below) indicated propylene conversions of 98.7 percent, per pass conversions to acrylo 80.2 percent, to HCN 5.0 percent, to acrolein 1.2 percent, to acrylic acid 1.8 percent from propylene. Notably, 10 to 13 percent of the feed ammonia was burning, with ammonia breakthrough of 0.06 g/scf and sulfuric acid usage in downstream quench operation of 0.07 gpm to neutralize excess ammonia. With no methanol (oxygenate) vapor injected, air was separately injected through air sparger at a position in the bed equal to 90 percent of the catalyst's expanded bed height, at dilute air to propylene molar ratio (DPAR) of 0.1, 0.2 and 0.3. An average of three recovery runs (Examples 12 to 14, Table 4, below) at increasing DPA ratios gave an average 99.2 percent $C_3=$ total conversion, 80.1 percent PPC to acrylo, 5.1 percent PPC to HCN, 1.1 percent PPC to acrolein, and 1.9 percent PPC to acrylic acid from propylene. Notably, 15 percent of feed ammonia was burned, and sulfuric acid usage dropped to 0.06 gpm (65 percent ABR) to 0.05 (71 percent ABR) to 0.04 (76 percent ABR) as dilute phase air addition was

TABLE 4

| Ex. No. | DPAR* mol air/ mol $C_3=$ | $H_2SO_4$ (gpm) | % ABR | $NH_3$ B.T. (g/scf) | Acrylo % PPC | HCN ($C_3=$) % PPC | Acrolein % PPC | Total $C_3=$ % | Total Air/$C_3=$ Ratio |
|---|---|---|---|---|---|---|---|---|---|
| Baseline | | | | | | | | | |
| 10 | 0 | .07 | 59 | .06 | 80.51 | 4.89 | 1.2 | 98.9 | 9.44 |
| 11 | 0 | .07 | 59 | .04 | 80.11 | 4.89 | 1.3 | 98.3 | 9.37 |
| Dilute Phase Air | | | | | | | | | |
| 12 | .1 | .06 | 65 | .03 | 80.39 | 4.96 | 1.2 | 99.3 | 9.43 |
| 13 | .2 | .05 | 71 | .05 | 80.07 | 5.15 | 1.1 | 99.2 | 9.54 |
| 14 | .3 | .04 | 76 | .05 | 79.95 | 5.15 | 1.1 | 99.2 | 9.31 |

EXAMPLES 15 TO 18

The next set of experiments was directed at lowering the bottom air/$C_3=$ molar ratio with increasing dilute phase air ratio, to see if the total air/$C_3=$ ratio could be lowered without penalizing AN or HCN yield while still reducing sulfuric acid consumption. At the same conditions of Examples 4 to 9, dilute phase air was injected at 90 percent of the catalyst's expanded bed height, at dilute air to propylene molar ratios of 0.2, 0.4 and 0.6, while decreasing the bottom air/$C_3=$ ratio from 9.1 to 8.9 to 8.7 to 8.6, respectively. In this way, the total air/$C_3=$ was kept approximately constant at 9.3 to 9.4. An average of three recovery runs (Examples 15 to 17, Table 5 below) at increasing DPA ratios gave an average 98 percent $C_3=$ total conversion, 80.4 percent PPC to acrylo, 4.8 percent PPC to HCN, 0.9 percent PPC to acrolein, and 1.4 percent PPC to acrylic acid from propylene. Notably, 15 percent of feed ammonia was burned, and sulfuric acid usage increased from 0.19 to 0.21 gpm, relative to baseline acid usage at 1.22 ammonia to propylene ratio. The relationship between dilute phase air to propylene ratio and sulfuric acid usage, all other reactor conditions being constant (e.g., bottom air/$C_3=$ ratio, $NH_3/C_3=$ ratio, catalyst bed temperature, reactor top pressure and catalyst inventory) was as follows:

TABLE 5

| Ex. No. | DPAR* mol air/ mol $C_3$= | $H_2SO_4$ (gpm) | % ABR | $NH_3$ B.T. (g/scf) | Acrylo % PPC | HCN ($C_3$=) % PPC | Acrolein % PPC | Total $C_3$= % | Total Air/$C_3$= Ratio |
|---|---|---|---|---|---|---|---|---|---|
| Baseline | | | | | | | | | |
| 14 | .0 | .17 | 0 | .18 | 80.90 | 5.08 | 0.72 | 98.9 | 9.46 |
| Dilute Phase Air | | | | | | | | | |
| 15 | .2 | 0.19 | −10 | .12 | 80.67 | 4.99 | 0.85 | 98.4 | 9.33 |
| 16 | .4 | 0.20 | −18 | .12 | 80.62 | 4.81 | 0.89 | 98.4 | 9.32 |
| 17 | .6 | 0.21 | −23 | .15 | 79.82 | 4.72 | 0.88 | 97.3 | 9.37 |

These experiments showed that total air/$C_3$= ratio could be kept constant, however, as the bottom air/$C_3$= was reduced, total $C_3$= conversion decreased which has a negative effect on HCN and AN yields. Further, sulfuric acid addition could not be reduced using dilute phase air addition in this manner. This showed that only a small reduction in the bottom air/$C_3$= ratio is possible without adversely affecting reactor product distributions and yields.

What is claimed is:

1. A method of reducing the amount of unreacted ammonia exiting the reactor during the manufacture of acrylonitrile comprising introducing into the lower portion of a fluid bed reactor ammonia, oxygen and a hydrocarbon selected from the group consisting of propylene and propane, to react in the presence of a fluid bed catalyst to produce acrylonitrile, introducing an additional amount of oxygen free of any oxygenate compound into the upper portion of the fluid bed reactor at a point where the additional oxygen does not substantially affect the reaction to produce acrylonitrile but reacts with at least some of the unreacted ammonia present in the reactor to reduce the amount of free ammonia present in the reactor effluent exiting said reactor, passing the reactor effluent containing acrylonitrile into a quench column to cool the reactor effluent with water to remove unwanted impurities and recovering the acrylonitrile from the quench column.

2. The process of claim 1 wherein the oxygen is introduced into the reactor in the form of air.

3. The process of claim 1 wherein the point of injection of the additional oxygen into the reactor is above at least 50 percent of the calculated expanded fluid catalytic bed height.

4. The process of claim 3 wherein the point of injection of the additional oxygen is above at least 70 percent of the calculated expanded catalytic bed height.

5. The process of claim 4 wherein the point of injection of the additional oxygen is above at least 90 percent of the calculated expanded catalytic bed height.

6. The process of claim 1 wherein the amount of additional oxygen injected into the reactor is sufficient to react with at least 15 percent of the unreacted ammonia.

7. The process of claim 1 wherein the amount of additional oxygen injected into the reactor is sufficient to react with at least 25 percent of the unreacted ammonia.

8. The process of claim 1 wherein the amount of additional oxygen injected into the reactor is sufficient to react with at least 40 percent of the unreacted ammonia.

9. The process of claim 1 wherein said hydrocarbon is propylene.

10. A method of producing acrylonitrile comprising introducing ammonia, oxygen and a hydrocarbon selected from the group consisting of propylene and propane into the lower portion of a fluid bed reactor containing a fluid bed ammoxidation catalyst to react in the presence of said catalyst to produce acrylonitrile wherein the improvement comprises introducing an additional amount of oxygen in the absence of any oxygenate compounds into the upper portion of the fluid bed reactor at a point where the oxygen does not substantially affect the reaction of the hydrocarbon, ammonia and oxygen containing gas to produce acrylonitrile but reacts with at least some of the unreacted ammonia present in the reactor to reduce the amount of ammonia exiting the reactor.

11. The method of claim 10 wherein the additional oxygen is injected into the upper portion of the reactor at a location above at least 70 percent of the calculated expanded fluid catalytic bed height.

12. The method of claim 10 wherein the additional oxygen is injected into the upper portion of the fluid bed reactor at a location above at least 80 percent of the calculated expanded fluid catalytic bed height.

13. The method of claim 10 wherein the additional oxygen is injected into the upper portion of the fluid bed reactor at a location above at least 90 percent of the calculated expanded fluid catalytic bed height.

14. The process of claim 10 wherein the amount of additional oxygen injected into the reactor is sufficient to react with at least 15 percent of the unreacted ammonia.

15. The process of claim 10 wherein the amount of additional oxygen injected into the reactor is sufficient to react with at least 25 percent of the unreacted ammonia.

16. The process of claim 10 wherein the amount of additional oxygen injected into the reactor is sufficient to react with at least 40 percent of the unreacted ammonia.

17. The process of claim 10 wherein said hydrocarbon is propylene.

18. A method of reducing the amount of unreacted ammonia exiting the reactor during the manufacture of acrylonitrile comprising introducing into the lower portion of a fluid bed reactor ammonia, oxygen and a hydrocarbon selected from the group consisting of propylene and propane, to react in the presence of a fluid bed catalyst to produce acrylonitrile, introducing an additional amount of oxygen into the upper portion of the fluid bed reactor at a point where the additional oxygen does not substantially affect the reaction to produce acrylonitrile but reacts with at least some of the unreacted ammonia present in the reactor to reduce the amount of free ammonia present in the reactor effluent exiting said reactor, passing the reactor effluent containing acrylonitrile into a quench column to cool the reactor effluent with water to remove unwanted impurities and recovering the acrylonitrile from the quench column.

* * * * *